United States Patent [19]
Makino et al.

[11] Patent Number: 5,520,929
[45] Date of Patent: May 28, 1996

[54] DIVISIBLE TABLET

[75] Inventors: Tadashi Makino; Yoshio Mizukami, both of Osaka; Shin-ichiro Hirai, Kyoto, all of Japan

[73] Assignee: Takeda Chemical Industries, Ltd., Osaka, Japan

[21] Appl. No.: 187,228

[22] Filed: Jan. 27, 1994

Related U.S. Application Data

[63] Continuation of Ser. No. 942,222, Sep. 9, 1992, abandoned.

[30] Foreign Application Priority Data

Sep. 10, 1991 [JP] Japan ............................... 3-081382 U

[51] Int. Cl.[6] ...................................................... A61K 9/44
[52] U.S. Cl. ............................ 424/467; 424/464; 424/474
[58] Field of Search .................................... 424/464, 467, 424/468

[56] References Cited

U.S. PATENT DOCUMENTS

| | | | |
|---|---|---|---|
| 3,883,647 | 5/1975 | Geller | 424/467 |
| 4,258,027 | 3/1981 | Ullman | 424/467 |
| 4,824,677 | 4/1989 | Shah et al. | 424/467 |
| 5,009,896 | 4/1991 | Becker | 424/467 |

FOREIGN PATENT DOCUMENTS

| | | |
|---|---|---|
| 0207888 | 1/1987 | European Pat. Off. . |
| 1246508 | 9/1971 | United Kingdom . |

Primary Examiner—Thurman K. Page
Assistant Examiner—William E. Benston, Jr.
Attorney, Agent, or Firm—Wenderoth, Lind & Ponack

[57] ABSTRACT

A tablet having first and second surfaces opposite to each other and a side surface lying perpendicular to any one of the first and second surfaces. A peripheral tablet edge delimited between each of the first and second surfaces and the side surface is chamfered to provide a respective inclined peripheral edge face over the entire perimeter of the tablet. This tablet also has at least a first generally V-sectioned score defined in the first surface so as to leave two tablet divisions of uniform size on respective sides of the V-sectioned first score. A pair of generally V-sectioned side scores are defined in the side surface of the tablet at respective locations opposite to each other and are continuous with opposite ends of the V-sectioned first score. The tablet can be divided along the V-sectioned score in the first surface by the application of a minimized finger pressure. The tablet of the invention is particularly suited to the pharmaceutical field.

15 Claims, 7 Drawing Sheets

Fig. 15
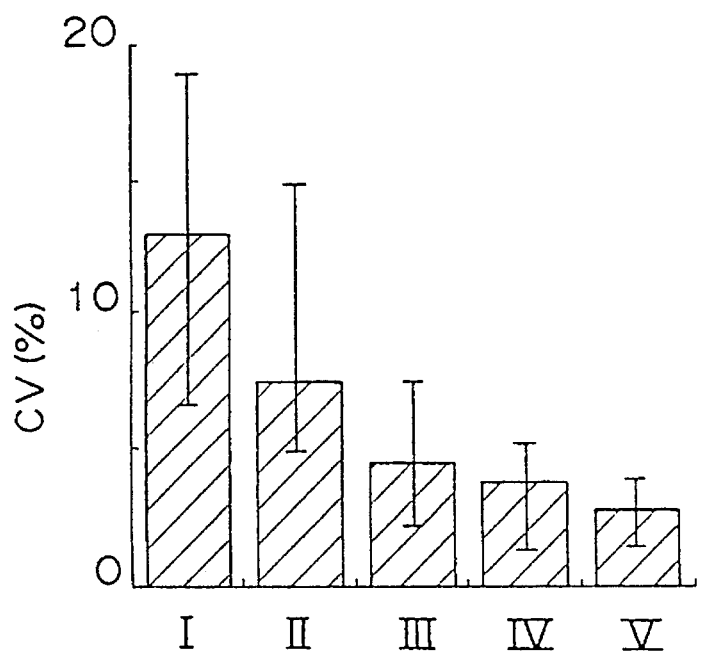
Fig. 16(a)
PRIOR ART
Fig. 16(b)
PRIOR ART
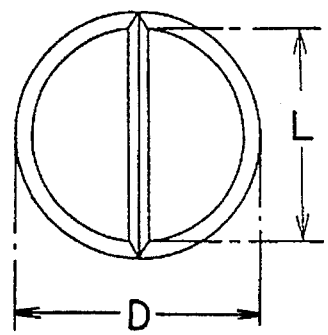
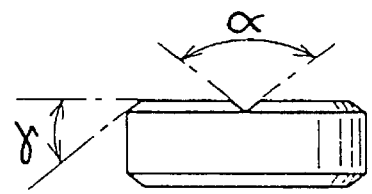

Fig. 17(a)   Fig. 17(b)
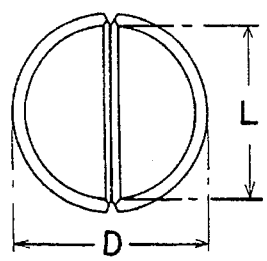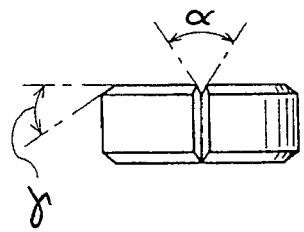
Fig. 18(a)   Fig. 18(b)
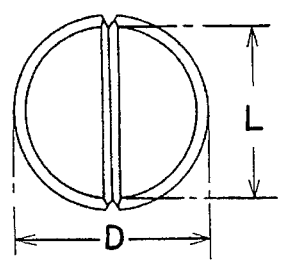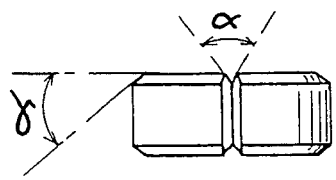
Fig. 19(a)   Fig. 19(b)
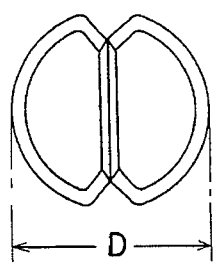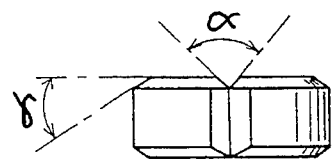
Fig. 20(a)   Fig. 20(b)
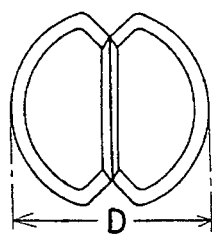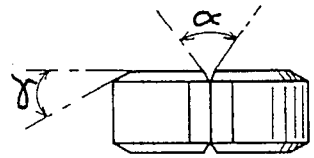

DIVISIBLE TABLET

This application is a continuation of now abandoned application, Ser. No. 07/942,222, filed on Sep. 9, 1992.

BACKGROUND OF THE INVENTION

1. Field of the Invention

The present invention generally relates to a tablet and, more particularly, to a divisible pharmaceutical tablet.

2. Description of the Prior Art

The divisible pharmaceutical tablet is not a new and recent development and has long been well known. The divisible pharmaceutical tablet has defined therein at least one score along which the tablet is divided into two tablet pieces by the application of a finger pressure. For example, the Japanese Laid-open Patent Publication No. 61-289027, published Dec. 19, 1986, (which in turn corresponds to the published European Patent No. A1-207,888, published Jan. 7, 1987), discloses a pharmaceutical tablet of a round shape having flat surfaces opposite to each other and also having at least one diametrically extending, generally V-sectioned score defined on at least one of the surfaces thereof. The surface of the round tablet where the V-sectioned score is defined has a pair of surface regions that are inclined inwardly from the circumferential tablet edge at an obtuse angle, for example, about 170 to 150 degrees, with respect to each other, each of said surface regions being inclined at an angle of about 5 to 15 degrees relative to the plane of the cross section of the tablet.

The round pharmaceutical tablet disclosed in the Japanese publication No. 61-289027 or European publication No. A1-207,888 is also featured in that the circumferential tablet edges opposite to each other are chamfered at an angle of about 20 to 40 degrees with respect to the plane of the cross section and that the V-sectioned score has an acute angle of, for example, 90 degrees and also has a depth generally equal to that of the chamfered circumferential tablet edge while the bottom of said V-sectioned score occupies a position no more than one third of the total depth of the tablet at the middle.

This prior art pharmaceutical tablet is indeed easy to divide when, while the tablet is placed on a support surface, for example, a table or a palm of a hand, with the V-sectioned score facing towards the support surface, an external pressure is applied to a center area of the tablet so as to act in a direction close towards the support surface. However, there may be a problem when the external pressure is applied in the wrong way, i.e., in a direction diagonally with respect to the plane of the cross section of the tablet. Once the external pressure is applied in the wrong way, a portion of the circumferential tablet edge may undesirably break or shatter, resulting in the tablet pieces of different size and, hence, dosage when the tablet is eventually divided along the V-sectioned score.

Japanese Laid-open Utility Model Publication No. 2-14333, published Jan. 29, 1990, discloses a pharmaceutical tablet having a right-angled peripheral edge on opposite surfaces thereof and also having a generally V-sectioned score defined on the opposite surfaces thereof in alignment with each other so as to leave symmetrical tablet pieces on respective sides of the V-sectioned score. The tablet disclosed therein is of a shape corresponding to the shape represented by two oval shapes adjoining to each other and also of a generally annular shape.

The second mentioned prior art pharmaceutical tablet is also easy to divide with no possibility of a portion of the peripheral tablet edge breaking or shattering even though the external pressure is diagonally applied. However, it appears that a portion of any of the peripheral tablet edges is susceptible to breakage under the influence of impacts which may be induced during transportation or storage of a batch of the pharmaceutical tablets. Once this occurs, the division of the pharmaceutical tablet results in the tablet pieces of different size and, hence, dosage, as is the case with the first mentioned prior art pharmaceutical tablet.

SUMMARY OF THE INVENTION

The present invention has been devised with a view to substantially eliminating the above discussed problems inherent in the prior art tablets and is intended to provide an improved tablet which is divisible without any accompanying breakage of a peripheral edge portion of the tablet to thereby ensure that the tablet pieces obtained by dividing the tablet are of uniform dosage.

To this end, and according to a broad aspect of the present invention, there is provided a tablet having first and second surfaces opposite to each other and a side surface lying perpendicular to the first and second surfaces. A peripheral tablet edge delimited between each of the first and second surfaces and the side surface is chamfered to provide a respective inclined peripheral edge face over the entire perimeter of the tablet. This tablet also has at least a first generally V-sectioned score defined in the first surface so as to leave two tablet divisions of uniform size on respective sides of the V-sectioned first score. A pair of generally V-sectioned side scores are defined in the side surface of the tablet at respective locations opposite to each other and are continuous with to opposite ends of the V-sectioned first score.

Preferably, the second surface of the tablet may also have a second generally V-sectioned score defined therein. In such case, opposite ends of the second V-sectioned score in the second surface are similarly continuous with to the side scores as is the case with the first V-sectioned score.

According to a further aspect of the present invention, there is provided a tablet having first and second surfaces opposite to each other and a side surface lying perpendicular to the first and second surfaces. A peripheral tablet edge delimited between each of the first and second surfaces and the side surface is chamfered to provide a respective inclined peripheral edge face over the entire perimeter of the tablet. This tablet also has at least first and second generally V-sectioned scores defined in the first surface so as to extend perpendicular to each other while leaving four tablet divisions of uniform size on respective quadrants defined by the first and second scores intersecting with each other. First and second pairs of generally V-sectioned side scores are defined in the side surface of the tablet with the side scores of the first pair being continuous with opposite ends of the first V-sectioned score and with the side scores of the second pair continuous with opposite ends of the second V-sectioned score.

In any event, each of the side scores has a depth which is preferably within the range of 7 to 20% of the length of the or each V-sectioned score on the first and/or second surfaces of the tablet. In this case, not only can the possibility be avoided that a premature breakage of the tablet along the V-shaped score may take place under the influence of impacts induced when the tablet embodying the present invention is packaged in PTP, when packages containing the tablets embodying the present invention are transported and/or when the tablet embodying the present invention is removed from the package, but also the tablet embodying the present invention can be easily and accurately divided into tablet pieces of equal dosage.

The presence of the pairs of the side scores is advantageous in that, when the tablet is desired to be divided into the two separate tablet pieces and, for this purpose, an external finger pressure is applied to a center area of the second surface of the tablet, a cracking is first initiated from the bottom of the V-sectioned score on the first surface of the tablet and then extends deep into the tablet while running in a direction substantially perpendicular to any one the opposite surfaces of the tablet, thereby ensuring the division of the tablet into tablet pieces of uniform size and, hence, equal dosage. In other words, the pairs of the side scores defined in the side surface of the tablet in opposition to each other serve to guide the cracking to take place in a direction substantially perpendicular to any one the surfaces of the tablet as accurately as possible.

BRIEF DESCRIPTION OF THE DRAWINGS

This and other objects and features of the present invention will become clear from the following description taken in conjunction with preferred embodiments thereof with reference to the accompanying drawings, in which like parts are designated by like reference numerals and in which:

FIG. 15 is a graph showing, for each of the sample tablets tested, a CV value of each of the tablets tested and the easiness of division of the respective tablets;

FIGS. 16(a) and 16(b) are top plan and side views of the prior art sample tablet tested, respectively;

FIGS. 17(a) and 17(b) are top plan and side views, respectively, of the tested sample tablets prepared according to an embodiment of the present invention.

FIGS. 18(a) and 18(b) are top plan and side views, respectively, of tested sample tablet prepared according to an embodiment of the present invention;

FIGS. 19(a) and 19(b) are top plan and side views, respectively, of tested sample tablet prepared according to an embodiment of the present invention; and FIGS. 20(a) and 20(b) are top plan and side views, respectively, prepared according to an embodiment of the present invention.

DETAILED DESCRIPTION OF THE EMBODIMENTS

Figure 1:
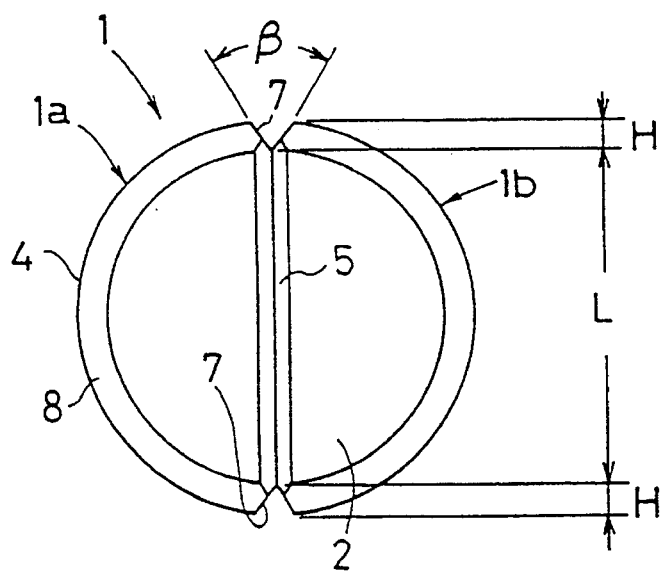
FIG. 1 is a top plan view of a tablet according to a first embodiment of the present invention.
Figure 2:
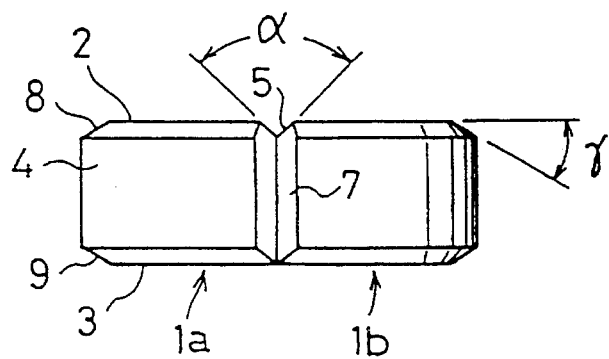
FIG. 2 is a side view of the tablet shown in FIG. 1.

Referring first to FIGS. 1 and 2, there is shown a pharmaceutical tablet 1 of a round configuration having a generally uniform thickness. This tablet 1 has top and bottom surfaces 2 and 3 opposite to each other and a peripheral side surface 4 lying perpendicular to the top and bottom surfaces 2 and 3. The tablet 1 includes a generally V-sectioned top groove 5 defined in the top surface 2 so as to eventually provide tablet pieces 1a and 1b of a substantially symmetrical shape when the tablet 1 is divided along the V-sectioned top groove 5 by the application of a finger pressure in any known manner. This V-sectioned top groove 5 has a groove angle α which is chosen to be about 90 degrees.

The illustrated tablet 1 also includes a pair of generally V-sectioned side grooves 7 defined in the peripheral side surface so as to extend completely across the thickness of the tablet 1 and also so as to extend perpendicular to the V-sectioned top groove 5 in the top surface 2 thereof while being continuous with respective opposite ends of the V-sectioned top groove 5. As a matter of course, the side grooves 7 are spaced 180 degrees circumferentially of the tablet 1. Each of the side grooves 7 has a depth H substantially equal to the depth of the top groove 5 and also has a groove angle β which is chosen to be about 70 degrees.

It is, however, to be noted that the depth H of each of the side grooves 7 is, in the illustrated instance, chosen to be about 7% of the length L of the top groove 5, which length L is defined as the maximum diameter of the tablet 1 less double the depth H of each V-sectioned side groove 7 as clearly indicated in FIG. 1.

As best shown in FIG. 2, circumferentially extending opposite edges of the tablet 1 adjacent the top and bottom surfaces 2 and 3 thereof are chamfered or bevelled to provide respective inclined edge faces 8 and 9 that extend in a slanted manner such that lines extending therefrom converge with each other at a point radially outwardly of the tablet 1. In the instance so far shown, the angle γ of inclination of each of the inclined edge faces 8 and 9 relative to the adjacent surfaces 2 or 3, respectively, of the tablet 1 is chosen to be about 30 degrees.

When the pharmaceutical tablet 1 of the design shown in and described with reference to FIGS. 1 and 2 is to be divided into two separate tablet pieces, a finger pressure should be applied to a center portion of the bottom surface 3 of the tablet opposite to the top surface 2 where the V-sectioned top groove 5 is defined, to allow the tablet 1 to be divided along the V-sectioned top groove 5. Because of the presence of the V-sectioned side grooves 7, a crack induced first from the bottom of the V-sectioned top groove 5 as the tablet 1 is divided by the application of the finger pressure in the manner described above can extend deep into the tablet while running in a direction substantially perpendicular to any one of the top and bottom surfaces 2 and 3, thereby ensuring the division of the tablet 1 into the tablet pieces 1a and 1b of uniform size and, hence, equal dosage. In other words, the pairs of the V-sectioned side grooves 7 in the side surface 4 of the tablet 1 are effective to ensure that the cracking takes place in a direction substantially perpendicular to any one of the surfaces of the tablet as accurately as possible so that the tablet pieces 1a and 1b of uniform-dosage can be eventually obtained.

Figure 3:
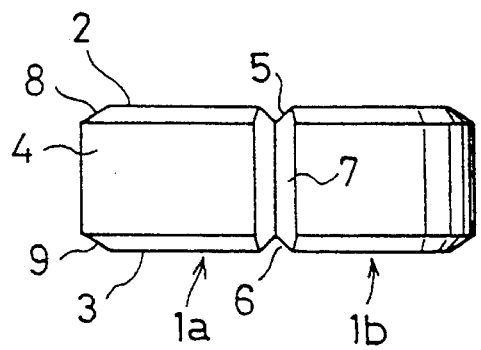
FIG. 3 is a side view of the tablet showing a modification of the tablet shown in FIGS. 1 and 2.

It is also to be noted that, as best shown in FIG. 3, the pharmaceutical tablet 1 discussed above may have an additional V-sectioned groove, i.e., a V-sectioned bottom groove 6, defined in the bottom surface 3 thereof in alignment with and parallel to the V-sectioned top groove 5. Where the two V-sectioned grooves 5 and 6 are defined in the top and bottom surfaces 2 and 3 of the tablet 1, respectively, the tablet 1 can be divided much easier than the tablet having the V-sectioned groove in only one surface thereof and, hence, requires a minimized pressure to be applied in dividing it into the tablet pieces.

Figure 4:
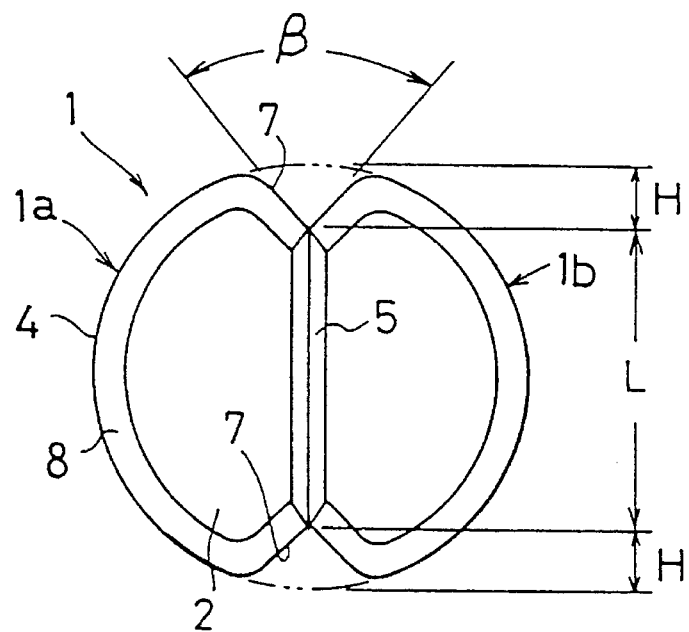
FIG. 4 is a top plan view of the tablet according to a second embodiment of the present invention.
Figure 5:
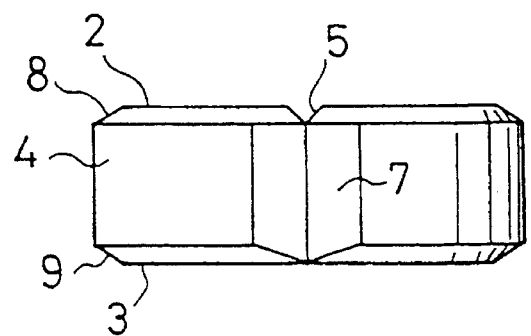
FIG. 5 is a side view of the tablet shown in FIG. 4.

A second embodiment of the present invention shown in FIGS. 4 and 5 differs from the first embodiment thereof shown in FIGS. 1 and 2 in that, in the second embodiment, the groove angle β is chosen to be 90 degrees and the depth H of each of the V-sectioned side grooves 7 is chosen to be about 20% of the length L of the V-sectioned top groove 5. It will readily be seen that, since the groove angle α and the groove depth H in the second embodiment of the present invention are greater than those in the first embodiment thereof, each of the tablet pieces 1a and 1b shown in FIG. 4 represents a shape closer to an oval shape than that represented by each tablet piece 1a and 1b shown in FIG. 1.

According to the second embodiment shown in FIGS. 4 and 5, the length L of the V-sectioned top groove 5, that is, the length of a joint between the tablet pieces 1a and 1b, can be optimized. Therefore, the tablet 1 according to the second embodiment advantageously requires a minimized pressure to be applied thereto to divide it into the tablet pieces 1a and 1b and, at the same time, any possible breakage of the tablet along the V-sectioned top groove 5 under the influence of impacts induced during packaging or filling thereof into a container can also be minimized.

Figure 6:
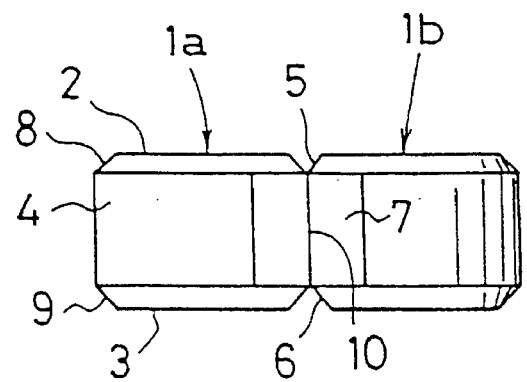
FIG. 6 is a side view of the tablet showing a modification of the tablet of FIGS. 4 and 5.

FIG. 6 illustrates a modification of the embodiment of FIGS. 4 and 5 wherein the tablet 1 shown in and described with reference to FIGS. 4 and 5 is modified to have a V-sectioned bottom groove 6 similar in dimension to the V-sectioned top groove 5 and extending diametrically in the bottom surface 3 in alignment with and parallel to the V-sectioned top groove 5.

According to the modification shown in FIG. 6, the use of the two V-sectioned grooves 5 and 6 on the top and bottom surfaces 2 and 3 has an extra advantage in that, when the tablet 1 is divided into the two tablet pieces 1a and 1b leaving a generally rectangular split face 10 in each tablet piece 1a and 1b, the respective split face 10 has its long sides inclined so as to continue, to associated fractions of the top and bottom surfaces 2 and 3. As shown in FIGS. 1–6 and as necessary to attain the generally rectangular split face 10, each of the V-sectioned grooves 5, 6 and 7 has a substantially uniform depth along its length. Considering that the circumferentially extending opposite edges of the tablet 1 adjacent the top and bottom surfaces 2 and 3 thereof are chamfered or bevelled to provide the respective inclined edge faces 8 and 9 as described in connection with the first embodiment of the present invention, each of the eventually divided tablet pieces 1a and 1b according to the modification of FIG. 6 has its peripherally extending opposite edges all chamfered or beveled enough to facilitate a deglutition by a patient or user.

Figure 7:
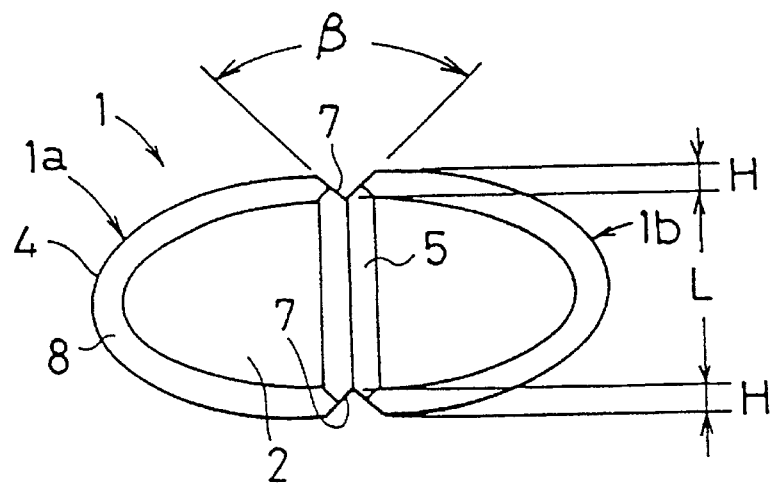
FIGS. 7 and 8 are top plan and side views of the tablet according to a third embodiment of the present invention.
Figure 8:
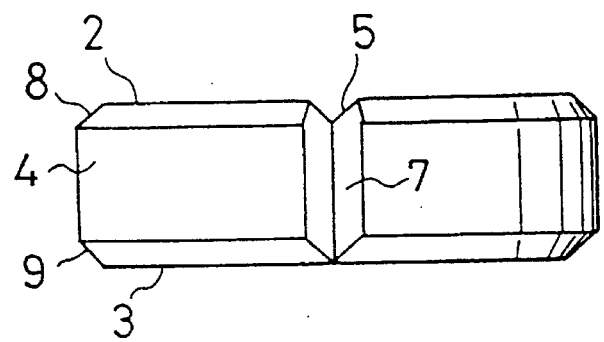

While the tablet 1 in any one of the foregoing embodiments has been described and shown as having a round shape, a tablet 1 according to a third embodiment of the present invention shown in FIGS. 7 and 8 has a substantially oval shape. As is well known to those skilled in the art, the oval shape has two geometrical axes, the minor and major axes perpendicular to each other. In the instance shown in FIGS. 7 and 8, the V-sectioned top groove 5 is defined in the top surface 2 of the tablet 1 so as to extend along the minor axis of the oval shape.

In this embodiment of FIGS. 7 and 8, each of the V-sectioned side grooves 7 has a groove angle β chosen to be within the range of about 90 to 100 degrees and also has a groove depth H chosen to be about 15% of the length L of the V-sectioned top groove 5.

Since the oval shape causes the V-sectioned top groove 5 to have a smaller length L when the top groove 5 is defined along the minor axis thereof, the pressure necessary to divide the tablet 1 along the top groove 5 into the tablet pieces 1a and 1b is further minimized advantageously.

Figure 9:
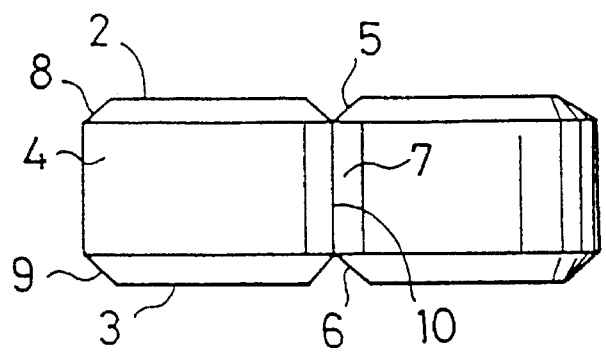
FIG. 9 is a side view of the tablet showing a modification of the tablet of FIGS. 7 and 8.

A modification shown in FIG. 9 is similar to the third embodiment shown in and described with reference to FIGS. 7 and 8 except that the tablet 1 shown in FIGS. 7 and 8 is modified to have a V-sectioned bottom groove 6 similar in dimension to the V-sectioned top groove 5 and extending in the bottom surface 3 in alignment with and parallel to the V-sectioned top groove 5.

Figure 10:
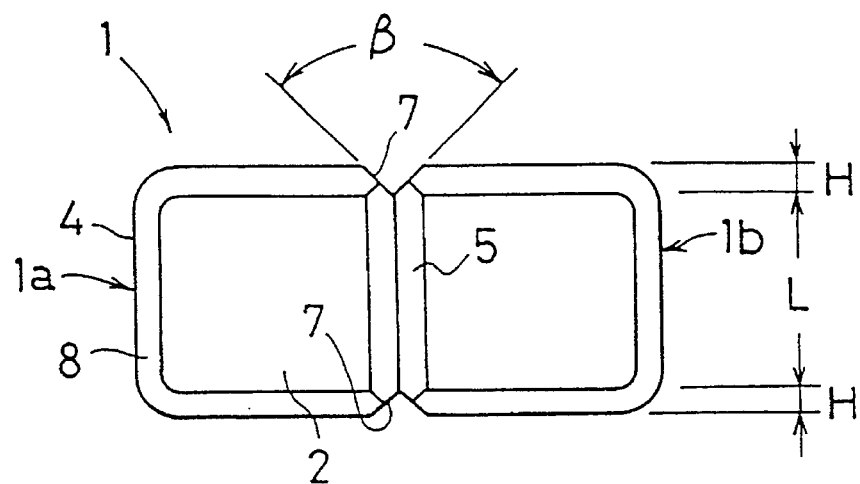
FIGS. 10 and 11 are top plan and side views of the tablet according to a fourth embodiment of the present invention.
Figure 11:
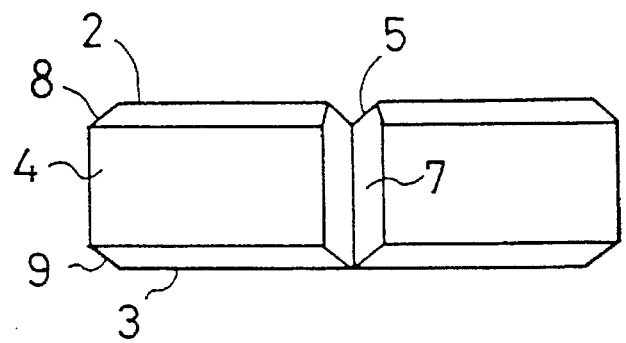
Figure 12:
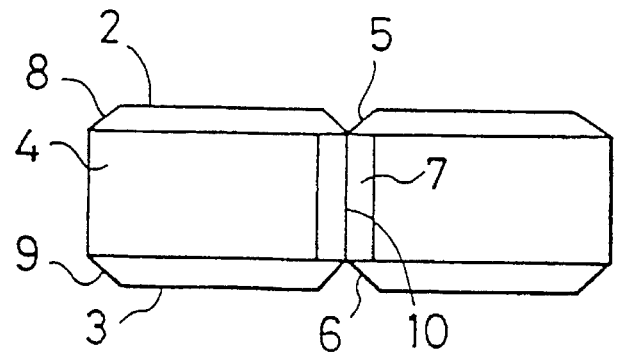
FIG. 12 is a side view of the tablet showing a modification of the tablet of FIGS. 10 and 11.

A pharmaceutical tablet of a generally rectangular shape is shown in FIGS. 10 to 12. According to a fourth embodiment of the present invention shown in FIGS. 10 and 11, the V-sectioned top groove 5 is defined in the top surface 2 of the tablet 1 so as to extend widthwise of the rectangular shape at a position intermediate of the length of the rectangular tablet 1. In this embodiment of FIGS. 10 and 11, each of the V-sectioned side grooves 7 has a groove angle α chosen to be about 90 degrees and also has a groove depth H chosen to be about 15% of the length L of the V-sectioned top groove 5, which length L extends, in this instance, in a direction widthwise of the rectangular tablet 1.

A modification shown in FIG. 12 is similar to the fourth embodiment shown in and described with reference to FIGS. 10 and 11 except that the tablet 1 shown in FIGS. 10 and 11 is modified to have a V-sectioned bottom groove 6 similar in dimension to the V-sectioned top groove 5 and extending in the bottom surface 3 in alignment with and parallel to the V-sectioned top groove 5.

While in each of the foregoing embodiments of the present invention, the surfaces of the tablet have been shown as having no more than a single V-sectioned groove, one or each surface of the tablet may have two V-sectioned grooves defined therein so as to extend perpendicular to each other.

Figure 13:
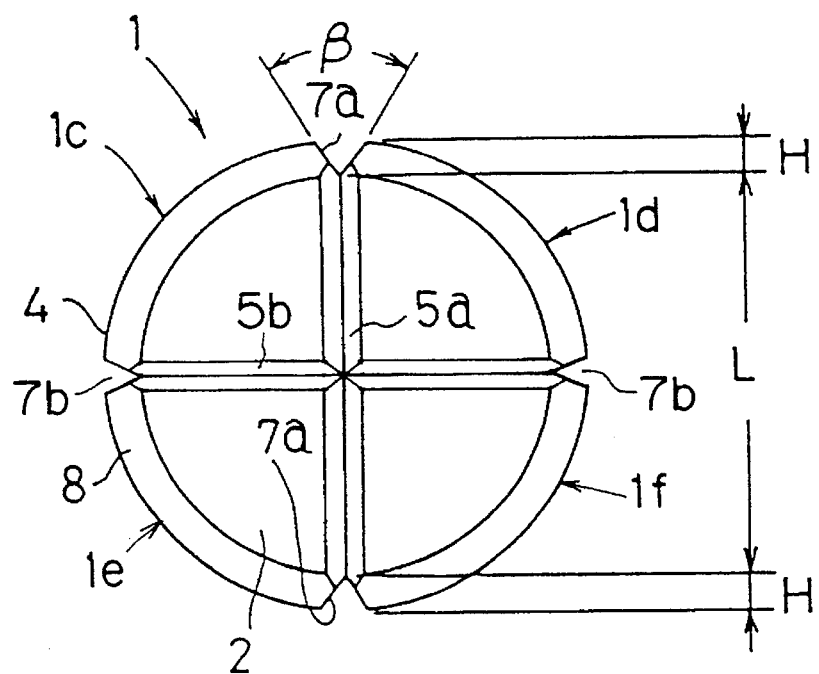
FIG. 13 is a top plan view of the tablet according to a fifth embodiment of the present invention.

Referring now to FIG. 13 showing the fifth embodiment of the present invention, the top surface 2 of the round tablet 1 is shown to have first and second V-sectioned top grooves 5a and 5b extending diametrically of the tablet 1, but perpendicular to each other. In correspondence with the use of the two V-sectioned top grooves 5a and 5b, the side surface 4 of the round tablet 1 has two pairs of V-sectioned side grooves 7a and 7b, the side grooves of one pair 7a being continuous with opposite ends of the top groove 5a and the side grooves of the other pair 7b being continuous with opposite ends of the top groove 5b.

Thus, it will readily be seen that the tablet 1 shown in FIG. 13 can be divided into four tablet pieces 1c, 1d, 1e and if of substantially equal dosage. If desired, the tablet 1 may be divided along one of the V-sectioned top grooves 5a and 5b to provide two tablet pieces of substantially equal dosage.

Figure 14:
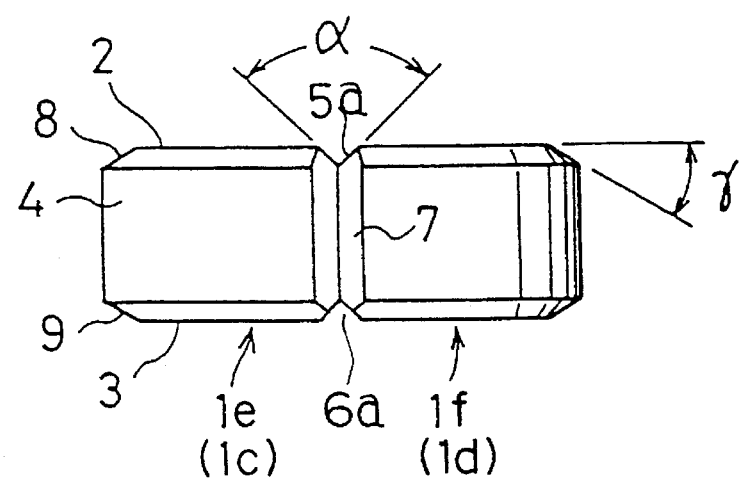
FIG. 14 is a side view of the tablet showing a modification of the tablet of FIG. 13.

As best shown in FIG. 14, the round table having the two V-sectioned top grooves 5a and 5b as shown in FIG. 13 may be modified to have two perpendicular V-sectioned bottom grooves (only one of which is shown by 6a in FIG. 14) defined in the bottom surface 3 in alignment with and parallel to the top grooves 5a and 5b, respectively.

In any event, the depth of each of the side grooves defined in the side surface of the, tablet is preferably chosen to be within the range of 7 to 20% of the length of the corresponding top groove so that the length of the joint between the tablet pieces that are eventually obtained by dividing the tablet remains greater than double the length of each side groove as measured along the direction of thickness of the tablet.

The inventors of the present invention have conducted a test to determine the easiness of division of the tablets according to the prior art and the present invention. FIG. 15 illustrates the CV value (Amount of change in weight of tablets) of the tablets tested. The CV value is calculated in terms of percentage of the difference in weight between the divided tablet pieces divided by half the weight of the tablet and is descriptive of the accuracy to which the tablet can be divided into the tablet pieces. The smaller the CV value, the more accurately the tablet can be divided into the tablet pieces of equal quantity. According to FIG. 15, it can be seen that samples (I and II were somewhat difficult to divide, whereas samples III–V were easily divisible.

TABLE 1

| Tablet Shape | Score Type | Size | CV Value Panelist Method | Bending Method |
|---|---|---|---|---|
| Round | Prior Art[1] | 8.0 mm | 8.1% | 10.7% |
| Round | FIG. 3 | 8.0 mm | 3.2% | 3.9% |
| Round | FIG. 3 | 6.5 mm | 4.8% | 4.2% |
| Oval | Prior Art[2] | 11 × 6 mm | 6.4% | 5.8% |
| Oval | FIG. 9 | 11 × 6 mm | 2.3% | 2.2% |

[Note: Round and oval tablets according to the prior art [1] and [2] have no side grooves.]

FIGS. 16 to 20 illustrate the sample tablets I to V employed in the tests. The sample tablet I shown in FIG. 16 is the prior art tablet having no side grooves employed, whereas the sample tablets II to V shown in FIGS. 17 to 20, respectively, are those prepared according to the present invention. All of those sample tablets has a 6 kg hardness and ten samples of each tablets I to V were examined by five panelists to determine the easiness of division, results of which are shown in the graph of FIG. 15.

It is clear from the table 1 above and the graph of FIG. 15 that, not only is the tablet according to the present invention easy to divide, but also the difference in weight between the divided tablet pieces is extremely small, as compared with the prior art tablet. In FIGS. 16–20 the angle of including γ of the inclined faces are γ=30°. Also in FIGS. 16–20, the angles ∝ are 100°, 90°, 90°, 90°, and 90°, respectively. Each of the samples shown in FIGS. 16–20 has a diameter D of 7.0 mm, whereas the sample of FIG. 16 has a dimension L of 6.0 mm. The dimension L for the FIG. 17 and 18 samples is 6.03 mm.

Although the present invention has been fully described in connection with the various embodiments thereof with reference to the accompanying drawings, it is to be noted that various changes and modifications are apparent to those skilled in the art. Specifically, although in the foregoing description of the preferred embodiments of the present invention, reference has been made to the pharmaceutical tablet, the concept of the present invention can be equally applicable to any divisible tablet in general such as used in any field other than the pharmaceutical field.

Accordingly, such changes and modifications are to be understood as included within the scope of the present invention as defined by the appended claims, unless they depart therefrom.

What is claimed is:

1. A pharmaceutical tablet which comprises a solid body having first and second surfaces opposite to each other and a peripheral side surface lying perpendicular to any one of the first and second surfaces, said solid body also having first and second peripheral edges each defined by and at an intersection between a corresponding one of said first and second surfaces and the peripheral side surface;

said first surface having at least one first V-sectioned score defined therein so as to extend across a center of said first surface;

said first peripheral edge at the intersection between the first surface and the peripheral side surface being chamfered over an entire perimeter thereof;

said second surface having at least one second V-sectioned score defined therein in a number equal to the number of the at least one first V-sectioned score and of a shape identical with that of the at least one first V-sectioned score so as to extend parallel to the at least one first V-sectioned score;

said second peripheral edge at the intersection between the second surface and the peripheral side surface being chamfered over an entire perimeter thereof;

said peripheral side surface having V-sectioned side scores defined therein at opposing peripheral positions, respectively, said V-sectioned side scores being respectively aligned with opposing ends of said first and second V-sectioned scores so as to be continuous therewith;

each of the V-sectioned side scores having a depth within a range of 7 to 20% of a length of each of the first and second V-sectioned scores with which the respective V-sectioned side score is aligned and continuous, the length of each of the first and second V-sectioned scores being defined as a maximum outer dimension of said tablet at a location adjacent the V-sectioned side scores and in a direction along the respective one of the first and second V-sectioned scores minus twice the depth of one of the V-sectioned side scores;

wherein said first and second V-sectioned scores, together with said V-sectioned side scores, constitute a means for dividing said solid body into first and second tablet pieces of substantially equal weight, each of which has opposing first and second tablet piece surfaces respectively defined by portions of said first and second surfaces of said solid body, such that all peripheral edges of each of said first and second tablet pieces are chamfered edges, including peripheral edges formed about an entire periphery of said first tablet piece surface, peripheral edges formed about an entire periphery of said second tablet piece surface, and peripheral edges formed about an entire periphery of a peripheral side surface formed upon division of said solid body into said first and second tablet pieces; and wherein each of said at least one first V-sectioned score and said at least one second V-sectioned score has a substantially uniform depth along its length.

2. The pharmaceutical tablet as claimed in claim 1, wherein said at least one first V-sectioned score comprises a pair of first V-sectioned scores defined in said first surface of said solid body, said at least one second V-sectioned score comprises a pair of second V-sectioned scores defined in said second surface of said solid body, and said V-sectioned side scores comprise first and second pairs of opposing V-sectioned side scores, said first pair of opposing V-sectioned side scores being aligned and continuous with one of said pair of said first V-sectioned scores and one of said pair of said second V-sectioned scores, and said second pair of opposing V-sectioned side scores being aligned and continuous with the other of said pair of said first V-sectioned scores and the other of said pair of said second V-sectioned scores; and said pair of said first V-sectioned scores and said pair of said second V-sectioned scores, together with said first and second pairs of V-sectioned side scores, constitute a means for dividing said solid body into four tablet pieces of substantially equal weight, each of which has opposing first and second tablet piece surfaces respectively defined by portions of said first and second surfaces of said tablet, such that each of said four tablet pieces has a chamfered edge formed about an entire periphery of said first tablet piece surface and a chamfered edge formed about an entire periphery of said second tablet piece surface.

3. The pharmaceutical tablet as claimed in claim 2, wherein depths of all of said V-sectioned side scores and said first and second V-sectioned scores are substantially equal.

4. The pharmaceutical tablet as claimed in claim 2, wherein an angle between confronting sides of each of said V-sectioned side scores is about 70 degrees;

an angle between confronting sides of each of said first and second V-sectioned scores is about 90 degrees; and depths of all of said V-sectioned side scores and said first and second V-sectioned scores are substantially equal.

5. The pharmaceutical tablet as claimed in claim 4, wherein each of said first and second surfaces of said solid body is substantially circular.

6. The pharmaceutical tablet as claimed in claim 4, wherein each of said first and second surfaces of said solid body is substantially oval.

7. The pharmaceutical tablet as claimed in claim 4, wherein each of said first and second surfaces of said solid body is substantially rectangular.

8. The pharmaceutical tablet as claimed in claim 1, wherein an angle between confronting sides of each of said V-sectioned side scores is about 70 degrees;

an angle between confronting sides of each of said first and second V-sectioned scores is about 90 degrees; and depths of all of said V-sectioned side scores and said first and second V-sectioned scores are substantially equal.

9. The pharmaceutical tablet as claimed in claim 8, wherein each of said first and second surfaces of said solid body is substantially circular.

10. The pharmaceutical tablet as claimed in claim 8, wherein each of said first and second surfaces of said solid body is substantially oval.

11. The pharmaceutical tablet as claimed in claim 8, wherein each of said first and second surfaces of said solid body is substantially rectangular.

12. The pharmaceutical tablet as claimed in claim 1, wherein depths of all of said V-sectioned side scores and said first and second V-sectioned scores are substantially equal.

13. The pharmaceutical tablet as claimed in claim 1, wherein each of said first and second surfaces of said solid body is substantially circular.

14. The pharmaceutical tablet as claimed in claim 1, wherein each of said first and second surfaces of said solid body is substantially oval.

15. The pharmaceutical tablet as claimed in claim 1, wherein each of said first and second surfaces of said solid body is substantially rectangular.

* * * * *